(12) United States Patent  (10) Patent No.: US 6,549,276 B1
Longtin  (45) Date of Patent: Apr. 15, 2003

(54) METHOD AND APPARATUS FOR OPTICAL MEASUREMENT OF CONCENTRATION AND TEMPERATURE OF LIQUIDS

(75) Inventor: Jon P. Longtin, East Setauket, NY (US)

(73) Assignee: Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 09/830,735

(22) PCT Filed: Oct. 30, 1998

(86) PCT No.: PCT/US98/23179

§ 371 (c)(1),
(2), (4) Date: Jul. 9, 2001

(87) PCT Pub. No.: WO00/26665

PCT Pub. Date: May 11, 2000

(51) Int. Cl.[7] .................................................. G01N 21/41
(52) U.S. Cl. ....................................... 356/128; 356/134
(58) Field of Search ............................... 356/128, 134, 356/335, 336, 337, 338, 341, 343, 388, 394

(56) References Cited

U.S. PATENT DOCUMENTS

| | | | | |
|---|---|---|---|---|
| 4,907,884 A | * | 3/1990 | Philips et al. ................ 356/336 |
| 5,129,723 A | * | 7/1992 | Howie et al. ................ 356/336 |
| 5,305,071 A | * | 4/1994 | Wyatt .......................... 356/128 |
| 5,548,393 A | * | 8/1996 | Nozawa et al. ............. 340/631 |
| 5,576,827 A | * | 11/1996 | Strickland et al. .......... 356/336 |
| 6,348,968 B2 | * | 2/2002 | Autrey et al. ................ 356/246 |

* cited by examiner

Primary Examiner—Michael P. Stafira
(74) Attorney, Agent, or Firm—Baker Botts L.L.P.

(57) ABSTRACT

Disclosed are a method and an apparatus for precision optical measurement of solute concentration and temperature of a transparent liquid. The apparatus includes a vessel (12) which contains a sample of liquid (14), the refractive index of which is to be determined, a light source (22) and a beam position sensor (30). The vessel (12) has an entrance side and an exit side, with a known angular relationship therebetween, and is situated in a known ambient The light source (22) is located so as to cause a beam of light to impinge on the entrance side at an angle with respect to a normal to an outer surface of the entrance side, to pass through the liquid (14), and to then pass through the exit side, from which it exits at an angle with respect to a normal to an outer surface of the exit side. The beam position sensor (30) provides data for determining the exit angle thereby permitting the refractive index of the liquid to be determined, based on the angles.

23 Claims, 4 Drawing Sheets

METHOD AND APPARATUS FOR OPTICAL MEASUREMENT OF CONCENTRATION AND TEMPERATURE OF LIQUIDS

STATEMENT OF GOVERNMENT RIGHTS

This invention was made with United States Government support under National Science Foundation Contract No. CTS-9702644. The United States Government may have certain rights in the invention as provided in the Contract.

FIELD OF THE INVENTION

The present invention relates to measurement of optical properties of materials, and, more particularly, to precision optical measurement of refractive index, concentration and temperature of materials.

BACKGROUND OF THE INVENTION

The precise measurement of concentration in liquids is important in fields such as chemical analysis and processing, diagnostics, semiconductor manufacturing, waste inspection, and measurement of liquid diffusion coefficients. Measurement of liquid temperature is also important, as is determination of the refractive index for both liquids and non-liquid materials. As such, a variety of techniques have been developed to measure concentration, temperature and/or refractive index. Bergman et al. developed a fiber-optic probe to measure salinity distribution in liquids, as described in T. L. Bergman, F. P. Incropera and W. H. Stevenson, "Miniature Fiber-Optic Refractometer for Measurement of Salinity in Double-Diffusive Thermohaline Systems," 56 *Rev. Sci. Instrum.* 291–96 (1985) and T. L. Bergman, D. R. Munoz, F. P. Incropera and R. Viskanta, "Measurement of Salinity Distributions in Salt-Stratified, Double-Diffusive Systems by Optical Deflectometry," 57 *Rev. Sci. Instrum.* 2538–41 (1986). Other techniques include a planar laser-induced fluorescence technique, as described in A Lozano, S. H. Smith, M. G. Mungal, and R. K. Hanson, "Concentration Measurements in a Transverse Jet by Planar Laser-Induced Fluorescence of Acetone," 32 *AIAA Journal* 218–21 (1993), and an invasive heat-marker method as described in V. A. Vink, G. A. Sokolov, and Yu. S. Fomochev, "Measurement of the Concentration of Flowing Liquid Solutions," 58 *Journal of Applied Chemistry of the USSR* 357–59 (1985). Interferometric techniques are described in T. Konishi, S. Naka, A. Ito and K. Saito, "Transient Two-Dimensional Fuel-Concentration Measurement Technique," 36 *Applied Optics* 8815–19 (1997), T. A. Wilson and W. F. Reed, "Low Cost, Interferometric Differential Refractometer," 61 *Am. J. Phys.* 1046–48 (1993) and R. J. Harris, G. T. Johnston, G. A. Kepple, P. C. Krok and H. Mukai, "Infrared Thermooptic Coefficient Measurement of Polycrystalline ZnSe, ZnS, CdTe, $CaF_2$, and $BaF_2$, Single Crystal KCI, and TI-20 Glas," 16 *Applied Optics* 436–38 (1977), and a phase-locked-loop ultrasonic method is described in K. Ikeda, "Ultrasonic Measurement of Concentration in Solutions by a Phase-Locked Loop Method," 36 *Jpn. J. Appl. Phys.* 3180–83 (1997).

Refractometers are routinely used to evaluate the refractive index to determine the concentration of a liquid mixture, as described in J. E. Geake, "Linear Refractometers For Liquid Concentration Measurement," *Chemical Engineer* 305–08 (1975). Still other techniques reported in the literature for accurately measuring the refractive index of solids and gases include the minimum deviation method as set forth in I. H. Malitson, "Refractive Properties of Barium Fluoride," *Journal of the Optical Society of America* 628–32 (1964) and B. C. Platt, H. W. Icenogle, J. E. Harvey, R. Korniski and W. L. Wolfe, "Technique for Measuring the Refractive Index and Its Change with Temperature in the Infrared," 65 *Journal of the Optical Society of America* 1264–66 (1975), the use of a Littrow prism as described in E. D. McAlister, J. J. Villa and C. D. Salzberg, "Rapid and Accurate Measurements of Refractive Index in the Infrared," 46 *Journal oft he Optical Society of America* 485–87 (1956) and A. R. Hilton and C. E. Jones, "The Thermal Change in The Nondispersive Infrared Refractive Index of Optical Materials," 6 *Applied Optics* 1513–17 (1967), Brewster angle techniques as described in I. K. Smirnov, Y. G. Polyakov and G. N. Orlov, "Arrangement for Measurement of Index of Refraction and Thickness of Transparent Dielectric Films by an Optical Method," *Journal of the Optical Society of America* 546–47 (1980), and others.

Examples of other techniques are set forth in S. M. Chernov, K. K. Zhilik and P. G. Rabzonov, "Determination of the Index Refraction of Liquids and Gases in Capillaries," 37 *Journal of Applied Spectroscopy* (English Translation of Zhurnal Prikladnoi Spektroskopii) 1069–72 (1982), L. A. Danisch, "Removing Index of Refraction Constraints in the Optical Measurement of Liquid level," *Fiber Optics and Laser Sensors X* 268–79 (1992) and D. R. Lide, Ed., *CRC Handbook of Chemistry and Physics* (CRC Press, Boca Raton, 1998). All of these techniques, however, suffer from one or more of the following shortcomings: direct contact is required with the material being measured, poor resolution is noted, complicated and expensive components are required, systems are physically large and difficult to operate, or a visual, subjective analysis of the data is relied upon.

In view of the foregoing deficiencies of currently known techniques for measurement of concentration and temperature in materials, including liquids, a need clearly exists for an apparatus and method for precision, non-contact measurement of concentration and temperature of a material, such as a liquid, where the apparatus and method does not require complicated and expensive components, is compact, easy to operate, and does not rely on visual, subjective readings of measurement data.

SUMMARY OF THE INVENTION

The present invention, which substantially overcomes the shortcomings of the currently known techniques, provides a method for determining the concentration and temperature of a transparent liquid. The method includes the steps of causing the liquid to be contained in a vessel having a transparent entrance side and a transparent exit side; causing a beam of light to impinge on the entrance side; and then calculating the refractive index of the liquid using Snell's law. In the step of causing the liquid to be contained in the vessel, the vessel can have an entrance side and an exit side with a known angular relationship therebetween, and can be immersed in known surroundings. In the step of causing the beam of light to impinge on the entrance side of the vessel, the impingement can be at an angle $\theta_i$ with the normal to an outer surface of the entrance side. The beam can then pass through the material, and then through the exit side, from which it exits at an angle $\theta_e$ with respect to the normal to an outer surface of the exit side impinged by the light beam.

The calculation of the refractive index of the material using Snell's law can be based on the angles $\theta_i$ and $\theta_e$, and can be done by applying Snell's law at the interface between the surroundings and the entrance side, the interface between the entrance side and the material, the interface between the material and the exit side, and the interface between the exit side and the surroundings.

The present invention also provides a method for determining the concentration of a given component (e.g., a solute) in a sample of a multi-component liquid mixture (e.g., a solution). The method includes the step of determining the refractive index of the sample of the multi-component liquid mixture as described above and then comparing the determined refractive index of the sample of the multi-component liquid mixture to predetermined data relating different concentrations of the given component of the multi-component liquid mixture to corresponding values of the refractive index of the multi-component liquid mixture. In this manner, the concentration of the given component of the sample of the multi-component liquid mixture can be determined from the refractive index of the sample of the multi-component liquid mixture determined as described above.

The present invention yet further provides a method for determining a change in concentration of a given component of a sample of a multi-component liquid mixture from an initial concentration of the given component which corresponds to an initial refractive index of the sample of the multi-component liquid mixture, at an initial sample temperature. The method includes determining an initial and a subsequent refractive index of the sample of the multi-component liquid mixture in the manner described above, and then determining a change in the refractive index by subtracting the initial refractive index from the subsequent refractive index. The method further includes measuring the initial and subsequent temperatures of the sample of the multi-component liquid mixture and then determining the change in the concentration of the given component in the sample of the multi-component liquid mixture from the initial concentration according to the following approximate formula:

$$\Delta C \cong (\Delta n - (\partial n/\partial T)\Delta T)(\partial n/\partial C)^{-1}, \quad (1)$$

where:

$\Delta n$ is the change in the refractive index of the sample, $\Delta C$ is the change in the concentration of the given component in the sample of the multi-component liquid mixture from the initial concentration, $\partial n/\partial T$ is partial derivative of index of refraction, n, of the multi-component liquid mixture, with respect to temperature, determined from known data (can be evaluated at sample temperature and is approximately constant for a $\Delta T$ up to 10–15° C., and can be treated as a function of temperature for larger temperature changes), $\Delta T$ is the difference between the subsequently measured temperature of the sample and the initial temperature, and $\partial n/\partial C$ is partial derivative of index of refraction, n, of the multi-component liquid mixture, with respect to concentration of the given component, evaluated from known data in a region near the initial concentration and near the sample temperature.

Also provided is a method for determining the temperature of a given sample of a liquid, which can be either a pure liquid or a multi-component liquid having a substantially constant concentration of the components. The method includes the step of determining the refractive index of the sample of the liquid as initially described above, and then comparing the refractive index of the sample of the liquid to predetermined data relating different temperatures of the liquid to corresponding values of the refractive index of the liquid. In this way, the temperature of the sample of the liquid can be determined which corresponds to the refractive index of the sample of the liquid which was determined as described above.

The present invention yet further provides an apparatus for determining the concentration of a solute and the temperature of a light transmitting liquid. The apparatus includes a vessel which contains the liquid, a light source, and a light beam position sensor. The vessel has a planar entrance side and a planar exit side with a known angular relationship therebetween, and is immersed in known surroundings. The light source is located so as to cause a beam of light to impinge on the entrance side at an angle $\theta_i$ with respect to the normal to the outer surface of the entrance side where the beam impinges, to pass through the material, and to then pass through the exit side, from which it exits at an angle $\theta_e$ with respect to the normal to the outer surface of the exit side where the beam exits. The sensor determines the exit angle $\theta_e$, thus permitting the refractive index of the material to be determined, based on the angles $\theta_i$ and $\theta_e$, by applying Snell's law. The application of Snell's law occurs at the interface between the surroundings and the entrance side, the interface between the entrance side and the material, the interface between the material and the exit side, and the interface between the exit side and the surroundings. The apparatus includes a computer which is suitably programmed to calculate the refractive index of the liquid, and to determine the unknown concentration or temperature of the liquid sample based on comparison with predetermined data.

The present invention thus provides methods and an apparatus capable of carrying out precision refractive index, concentration and temperature measurement of liquids. The apparatus and methods overcome the disadvantages of prior systems and methods. In particular, the present method and apparatus permit real time, non-invasive, remote measurements with high resolution and can be carried out using simple and inexpensive components. Further, the apparatus is compact and easy to operate. Yet further, measurements can be based on readily quantifiable and measurable parameters, rather than visual, subjective parameters. Real-time remote monitoring of liquid component concentration, such as real-time mixture monitoring, precision solute and contaminant analysis, and measurement of diffusion coefficients of components of a multi-component liquid mixture, for example, are all possible with the present invention.

These and other features and advantages of the present invention will be pointed out in the following specification, taken in connection with the accompanying drawings, and the scope of the invention will be set forth in the appended claims.

DETAILED DESCRIPTION OF THE INVENTION

Figure 1A:
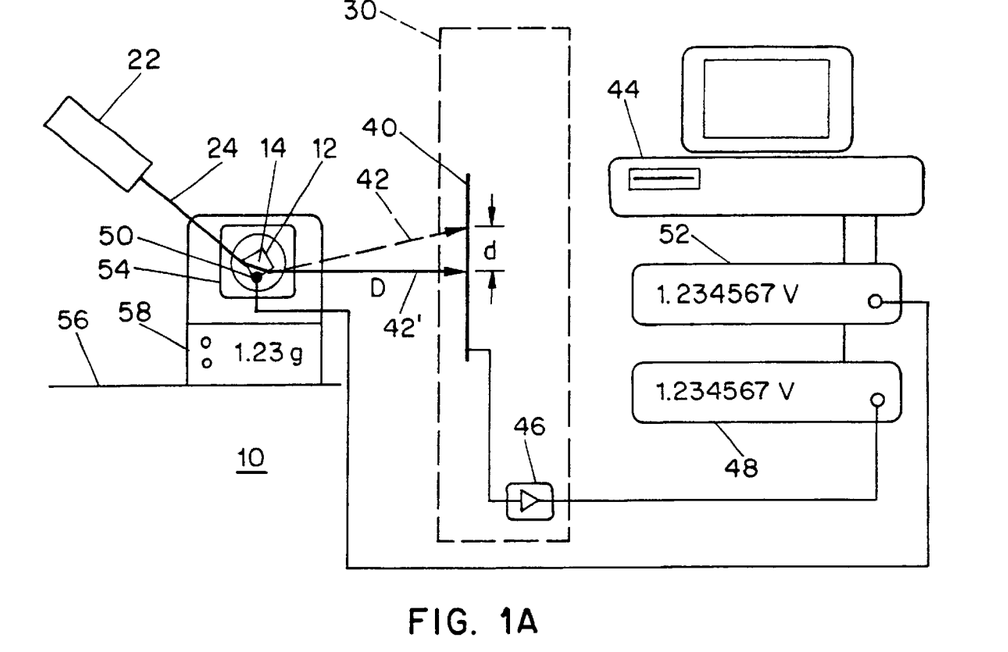
FIG. 1A is a schematic diagram of an exemplary embodiment of an apparatus according to the present invention.
Figure 1B:
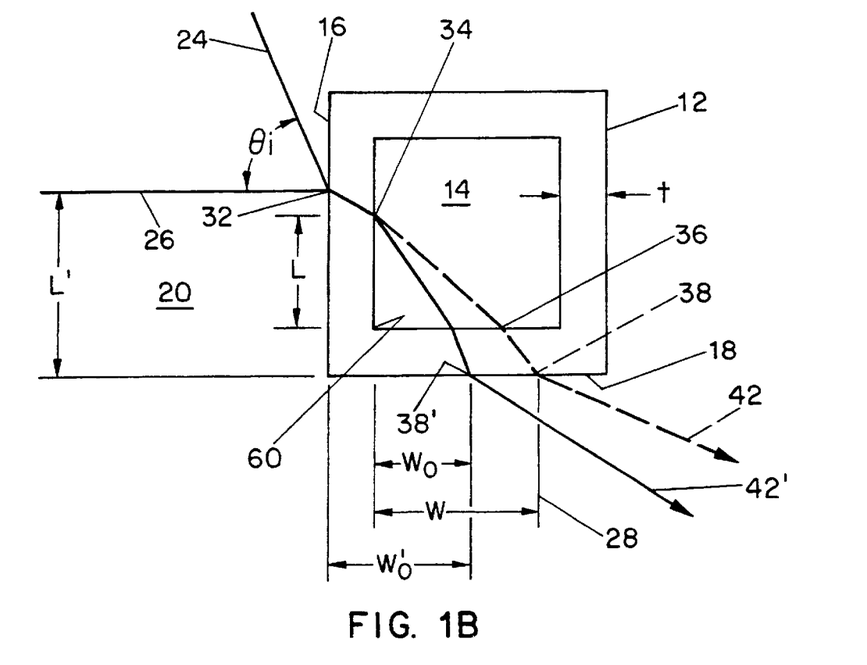
FIG. 1B is a detailed view of a vessel of the apparatus of FIG. 1A, showing various parameters of interest.

Reference should now be had to FIGS. 1A and 1B for a description of the exemplary embodiments of the apparatus and method of the present invention. An exemplary apparatus for determining the refractive index of a material, according to the present invention, is designated generally by reference numeral 10. The apparatus includes a vessel 12 which contains a multi-component liquid 14 (e.g., a solution). As best seen in FIG. 1B, the vessel 12, which can be, for example, a precision cuvette, has a planar entrance side 16 and a planar exit side 18. The vessel 12 can be immersed in known surroundings 20, such as ordinary atmospheric air.

Referring again to FIG. 1A, the apparatus 10 also includes a laser light source 22 which is located so as to cause a collimated beam of coherent light 24 to impinge on the entrance side 16 at an angle $\theta_i$ with respect to a normal 26 to the outer surface of the entrance side 16 where the light beam impinges. Light source 22 is located with respect to vessel 12 such that beam 24 then passes through the liquid 14 and then through the exit side 18, from which it exits at an angle $\theta_e$ with respect to a normal 28 to the outer surface of the exit side 18 where the beam exits.

Apparatus 10 further includes a beam position sensor, designated generally as 30, which determines the exit angle $\theta_e$, thus permitting the refractive index of the material 14 to be determined, based on the angles $\theta_i$ and $\theta_e$, by using Snell's law. In particular, Snell's law is applied at an interface 32 between the surroundings 20 and the outer surface of the entrance side 16, an interface 34 between the inner surface of the entrance side 16 and the liquid 14, an interface 36 between the liquid 14 and the inner surface of the exit side 18, and an interface 38 between the outer surface of the exit side 18 and the surroundings 20.

It should be noted that the vessel 12 need not necessarily be completely filled with the liquid 14, it is only necessary that liquid 14 be present in sufficient quantity to contain the path of the beam of light 24. Further, it will be appreciated that the light source can be a laser, so as to provide a collimated beam of coherent light 24, and that the laser may be a helium-neon laser having a wavelength of 632.8 nm. Of course, other types of light sources emitting collimated light beams at other wavelengths can be employed.

As noted, the planar entrance side 16 and the planar exit side 18 of the vessel 12 have a known angular relationship between them, such that Snell's law can be applied. The entrance and exit sides 16, 18 may be perpendicular, so as to make various calculations simpler, as will be apparent below. Sensor 30 preferably includes a light beam position sensor 40 which senses a position of the beam of light 24 after the beam exits the exit side 18 of the vessel 12. The beam is designated as 42 in this region. Position sensor 40 preferably has a known geometrical positional relationship to the vessel 12 so that the sensed position of the beam 42 can be related to the exit angle $\theta_e$. In a simple form of the invention, the beam position sensor 40 can simply be a suitable flat surface wherein the position of illumination by the beam 42 can be detected and related to an initial position. In a preferred form, a semiconductor beam position sensor, to be discussed below, is employed.

It is envisioned that the present invention will have particular utility for measurements of temperature and concentration to be carried out with materials 14 which are in the liquid phase. Measurement of index of refraction of gases may be accomplished by containing the gases in a sealed vessel at a desired pressure (in practice, the near-unity index of refraction of most gases may limit the utility of the method except, possibly, at high pressures).

The entrance and exit sides 16, 18 of the vessel 12 preferably have a substantially uniform thickness, t, as shown in FIG. 1B, and are preferably made from the same light transmitting material such that they have substantially the same refractive index. Although the dimension t is shown on a side of the vessel other than the entrance and exit sides 16, 18 in FIG. 1B, it will appreciated that only these particular sides need have the uniform thickness and refractive index to obtain the desired benefits. However, in a precision optical cuvette, all sides are uniformly thick and have a substantially uniform refractive index, and it is such a cuvette which is envisioned as being one preferred form of vessel for use with the present invention.

The apparatus 10 can also include a computer 44 which receives a representation of the position of the beam 42 of coherent light and which determines the refractive index of the liquid 14, according to the following equation:

$$d(n_1) = [W_0 - W(n_1)]\cos\theta_{e,0} + \{D - [W_0 - W(n_1)]\}\tan[\theta_e(n_1) - \theta_{e,0}] \quad (2)$$

where:

$d(n_1)$ is the position of said beam of light 42, measured with the position sensor 40, relative to an initial calibration value (which can be measured with a test liquid, as discussed below), $W_0$ is a reference value of distance between an inner corner 60 formed by the intersection of the planar entrance and exit sides 16, 18, and a point where the beam of light 42' exits the exit side 18 (see interface 38'), determined by measurement and calculation, as discussed below, $\theta_{e,0}$ is a reference value of the angle at which the beam of light 42' exits the exit side 18, determined during calibration, D is distance from the point where the beam of light exits the exit side to the position sensor 40, measured during calibration, $W(n_1)$ is a value of the distance between the inner corner 60 formed by the intersection of the entrance and exit sides 16, 18, and a point where the beam of coherent light 42 exits the exit side 18 when the vessel 12 contains the liquid being measured, during a given measurement, defined according to the equation:

$$W(n_1) = L \cot[\arcsin((\sin\theta_i)/n_1)] + t\tan\{\arcsin[(n_1/n_g)(1-(\sin\theta_i)/n_1)^{1/2}]\} \quad (3)$$

where:

L=distance from the inner corner 60 to a point where the beam of light passes from the entrance side into the liquid (interface 34), determined by measurement and Snell's-law calculation, $n_1$=refractive index of liquid which is to be determined, t=thickness of vessel walls, and $n_g$=refractive index of vessel walls, and $\theta_e(n_1)$ is the value of $\theta_e$, during measurement of a given liquid, defined according to the equation:

$$\theta_e(n_1) = \arcsin\{n_1 \cos[\arcsin((\sin\theta_i)/n_i)]\}. \quad (3)$$

It will be appreciated that equations (2), (3) and (4) hold for both positive and negative values of $d(n_1)$. Further, it will be appreciated that a neat, explicit solution for d($n_1$) is not available so that equations (2), (3) and (4) can be solved, for example, by manual or computer-aided iterative calculation.

The position sensor 40 is preferably a semiconductor light beam position sensor, such as a photodiode beam position sensor to be further described below, coupled to a position-to-voltage converter 46 which produces an output voltage which is substantially linearly proportional to the displacement of the beam 42 from its reference position 42' determined during calibration. Further, computer 44 is preferably a general purpose digital computer, although those of skill in the art will appreciate that an application specific integrated circuit (ASIC) can also be employed. Apparatus 10 can further include a first digital voltmeter 48 which receives the output voltage from the position-to-voltage converter 46 and which supplies a corresponding digital signal to the computer 44 as the aforementioned representation of the position of the beam of light 42.

Apparatus 10 can further include a temperature sensor 50 which is positioned to sense the temperature of the liquid 14 and which is coupled to the computer 44 so as to supply the computer 44 with a digital signal representative of the temperature of the liquid 14. The coupling between the temperature sensor 50 and the computer 44 can be, for example, a second digital voltmeter 52. Sensor 50 is preferably a thermistor, but could also be a thermocouple, or any other type of suitable temperature sensor known to those of skill in the art.

Apparatus 10 can also include a rotation stage 54 on which the vessel 12 is mounted. Rotation stage 54 permits the angle of incidence of the beam of light 42 onto the vessel 12 to be adjusted during calibration of the apparatus 10, such that the reference position of the beam from the exit side 18 of the vessel 12 during calibration is substantially perpendicular to the plane of the beam position sensor 40 and impinges the sensor 40 at its midpoint. The beam 42' shown in FIGS. 1A and 1B represents a reference beam during a calibration process, which has been adjusted to be substantially perpendicular to the beam position sensor 40, and will be described more fully below.

For purposes of validation and calibration, apparatus 10 can further include a scale 58 interposed between the rotation stage 54 and a mounting surface 56. Scale 58 is preferably a digital balance. It can be provided in order to determine the mass of the liquid 14 being measured, and particularly changes in mass concentration of a liquid being measured, by weighing samples of the liquid 14 contained in the vessel 12 as additional mass of a given component is added to change the concentration. Again, the scale is not normally envisioned for use in a production environment, since the apparatus of the present invention would be employed to determine concentration.

It should be noted that concentration of a component in a multi-component liquid may be expressed in molar, volume percent or mass percent units in accordance with the present invention, however, mass percent is considered to be preferable.

The apparatus of the present invention can be employed to determine the unknown temperature of a sample of liquid 14 by measuring its index of refraction. The index of refraction of the material 14 can then be compared to predetermined data which relate different temperatures of the material to corresponding values of the refractive index of the material. Thus, the temperature, hitherto unknown, can be determined for a given sample of liquid by measuring the refractive index of the sample and converting the measured refractive index to a corresponding sample temperature. Computer 44 can be programmed to carry out such calculations, although they can also be done manually. Temperature determination is most practical for pure materials, or for multi-component materials having a substantially constant concentration of the components. The refractive index of the unknown material is measured, and is then compared to known values of temperature vs. index of refraction, for example, using interpolation, a curve fit, or any other suitable means which will be apparent to those of skill in the art. Straight line, polynomial or spline curve fits can be employed. The "Tablecurve 2D" program available from SPSS software has been found to be useful for such curve fitting.

The apparatus 10 according to the present invention can also be used to determine the unknown concentration of a given component of a multi-component liquid mixture. In this case, the liquid 14 is a multi-component liquid mixture and the determination is carried out by comparing the measured refractive index of the multi-component liquid mixture to predetermined data which relate different concentrations of the given component of the multi-component liquid mixture to corresponding values of the refractive index. Again, this comparison can be carried out manually, or preferably by a suitably programmed computer 44. Thus, an unknown value of the concentration of a given component of a sample of the multi-component liquid mixture can be determined by measuring the refractive index of the sample and converting the measured refractive index to a corresponding concentration of the given component in the sample of the multi-component liquid mixture. Again, as for temperature, a suitable interpolation between tabulated values, comparison with a curve fit, or any other desired method can be employed.

As will be discussed more fully below, the refractive index of a multi-component liquid mixture is a function of the mixture temperature, mixture component concentration, and wavelength of the incident light. While the wavelength of the incident light is substantially constant when using a laser, the temperature and concentration can vary. When it is desired to determine the concentration of a given component in the mixture, in the presence of temperature changes, suitable correction must be carried out. For relatively large changes in concentration, values of refractive index as a function of concentration can be stored in computer 44 (or otherwise) for a number of different values of temperature. The measured refractive index of the specimen of unknown concentration can then be compared to predetermined data for at least two temperatures nearest the temperature of the specimen, which can be measured with the temperature sensor 50. Interpolation can then be carried out between the values of the predetermined data at the at least two nearest temperatures so as to obtain the value of the concentration of the given component of the liquid 14 for the actual temperature of the liquid 14. An ordinary bilinear interpolation, familiar to thermodynamics students who have used the steam tables for the properties of water vapor, can be employed and can be programmed into computer 44, as will readily be appreciated by those of skill in the art. Other suitable interpolation methods employing curve fitting and the like can also be used.

Figure 3:
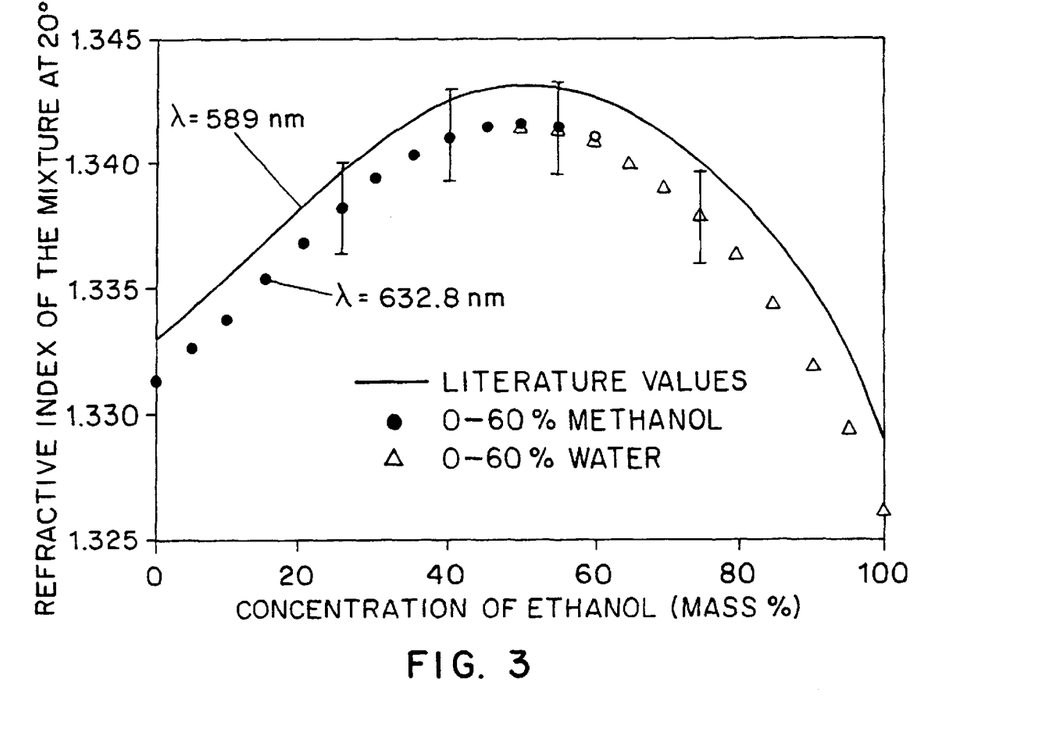
FIG. 3 is a figure similar to FIG. 2 for a methanol-water mixture.

Reference should now be had to FIG. 3, which will be discussed in greater detail below. Note that in some liquid mixtures, for example, the methanol-water mixture shown in FIG. 3, a given value of the refractive index of the mixture can correspond to two different values of concentration. In this case, if no other information is known, a unique value of concentration for a given a measured value of refractive index cannot be determined. However, if the previously measured values of concentration, which indicates a range of expected concentrations are available, then the correct value of the concentration can be selected. For example, computer 44 could be programmed to store values of the concentration of the given component of the liquid taken at previous proximate points in time and to employ the previous values to select the correct value of the concentration when the concentration is double valued with respect to the index of refraction.

Still referring to FIG. 3, for example, consider the dark dots which represent a first series of measurements carried out from 0 mass % methanol through 60 mass % methanol. Suppose, for an industrial process, it was known that the initial refractive index was about 1.331 for an initial methanol concentration of 0 mass %. Further, suppose that measurements of indices of refraction were made every 10 seconds, and the next two measurements yielded refractive indices of approximately 1.332 and 1.333, which according to the data in FIG. 3 could correspond to about 5 and 10 mass % methanol, respectively, or to about 84 and 83 mass % methanol, respectively. Assuming that it is known that the concentration of methanol increases relatively slowly with time (and in the absence of radical jumps or piecewise discontinuities in the relationship between n and C), it may be inferred that 5 and 10 mass % are the correct methanol concentrations corresponding to the refractive index measurements of 1.332 and 1.333, respectively. When a value of 1.335 was measured as the refractive index approximately 10 seconds later, based on the previous data, it may be inferred that this corresponded to a 15 mass % concentration of methanol (instead of 82 mass %), according to the data in FIG. 3. Other methods of dealing with double-valued systems are possible, such as deliberately introducing a small increase in concentration of a given component (e.g., methanol) and measuring a change in the index of refraction. An increase means the left side of curve in FIG. 3 while decrease means the right side of curve. A decrease in concentration could also be introduced to determine which side of the n vs. C curve should be used to indicate the concentration corresponding to a measured value of refractive index. Thus, the slope of the n vs. C curve is used to resolve the double—valued problem.

As noted, the apparatus 10 can be used for measurement of a multi-component liquid 14. Further, apparatus 10 can also include the aforementioned computer 44 and the aforementioned temperature sensor 50 which, as noted, can be positioned to sense temperature of the multi-component liquid 14 and which can be coupled to the computer 44 so as to supply the computer with a signal which is representative of the temperature of the multi-component liquid 14. When it is expected that relatively small concentration changes will be encountered, the apparatus 10 can be used to calculate changes in the concentration of given components of the multi-component liquid mixture from an initial value. Computer 44 can be programmed to determine the refractive index of a sample of the multi-component liquid mixture based on the entrance and exit angles $\theta_i$ and $\theta_e$, by applying Snell's law at the interfaces 32, 34, 36, 38 as discussed above. Computer 44 can further be programmed to determine a change in the refractive index of the multi-component liquid mixture by subtracting, from the refractive index determined by the computer, an initial refractive index of the sample of the multi-component liquid mixture corresponding to an initial concentration of a given component at a given temperature measured with the temperature sensor 50.

Computer 44 can be further programmed to receive the signal which represents the temperature of the given sample of the multi-component liquid mixture, and to determine the change, $\Delta C$, in the concentration of the given component of the sample of the multi-component liquid mixture from the initial concentration according to Equation (1) above. Equation (1) is advantageously used in cases where $\Delta C$ is relatively small. As a rule of thumb, Equation (1) is appropriately used for up to 5 or even 10% changes in C, although for substantially constant values of $\partial n/\partial c$ (at a constant temperature), Equation (1) can be used for almost any value of $\Delta C$.

In view of the foregoing description, it will be appreciated that the apparatus 10 can be employed to measure the index of refraction of a liquid, the temperature of a liquid, the concentration of a given component in a multi-component liquid, or a change in concentration of a given component in a multi-component liquid. In all cases where various calculations are referred to as being performed by computer 44, it will be appreciated that they could also be performed manually or by any other known means.

A method, according to the present invention, for determining the refractive index of a liquid 14, will now be discussed. The method includes the steps of (a) causing the material to be contained in a vessel 12 having an entrance side 16 and an exit side 18 of known refractive index; (b) causing a beam of coherent light 24 to impinge on the entrance side 16 at an angle $\theta_i$ with respect to a normal 26 to the surface of the entrance side 16 where the beam impinges; and (c) calculating the refractive index of the liquid 14.

In step (a), as for the apparatus 10, the vessel 12 can have entrance and exit sides 16, 18 with a known angular relationship therebetween and can be immersed in known surroundings 20. In step (b), the beam of light 24 can pass through the liquid 14, and then through the exit side 18 of the vessel 12, from which it exits at an angle $\theta_e$ with respect to a normal 28 to the surface of the exit side 18 where the beam exits. The angle $\theta_e$ can be measured directly or indirectly within the scope of the present invention. The refractive index of the material can then be calculated based on the angles $\theta_i$ and $\theta_e$, by applying Snell's law at the interfaces 32, 34, 36, 38, as described discussed above.

In a case where the liquid 14 is a multi-component liquid mixture, a further step (d) can be performed, which comprises repeating steps (a) through (c) for samples of the multi-component liquid mixture having different concentrations of a given component. Accordingly, a curve of values of the refractive index of the multi-component liquid mixture corresponding to different concentrations of a given component can be obtained. Such curves are shown, for example, in FIGS. 2 and 3 and will be discussed further below. Throughout this application, "curve" should be understood broadly to include a physical, graphical plot, tabulated data values, parameters stored in a computer, and the like. Yet further, step (d) can be repeated under substantially isothermal conditions at a plurality of different temperatures, so as to obtain a family of curves of values of the refractive index of the multi-component liquid mixture corresponding to different concentrations of a given component for the plurality of different temperatures. For example, a family of curves similar to FIG. 2 could be obtained at temperatures other than 20° C. The data obtained by this method could then be used, for example, by computer 44, to determine the unknown concentration of a given sample by measuring its index of refraction and, optionally, temperature.

In another aspect of the invention, the liquid 14 can be either a pure liquid or a multi-component liquid mixture having a substantially constant concentration of its components. An additional step can be performed in this case, of repeating steps (a) through (c) for samples of the liquid at different temperatures, so as to obtain a curve of values of the refractive index of the liquid corresponding to different temperatures of the liquid. While such a curve is not shown in the drawing figures herein, it will represent a plot of refractive index versus temperature for either a pure liquid or a multi-component liquid mixture where the concentrations of all the components are constant. Further discussion on the refractive index as a function of temperature, concentration and wavelength will be presented below. However, as used herein, "substantially constant concentration" means that any changes in concentration of the components are small enough such that they may be neglected in determining a change in the refractive index.

The method can also include the step of providing an beam position sensor 40 as discussed above, which senses a position of the beam of light 42 following exit from the exit side 18. Just as for the vessel 12, the entrance and exit sides 16, 18 can be substantially perpendicular. Sensed position from the beam position sensor 40 can be used in calculating the refractive index.

As noted with respect to the vessel 12 the entrance and exit sides 16, 18 of the vessel 12 can have a substantially uniform thickness, such as t, and a substantially uniform refractive index. Step (c) can include determining the refractive index of the liquid sample 14 according to equations (2), (3) and (4) set forth above.

It is desirable that apparatus 10 be calibrated before use, and one possible method of performing such calibration will now be discussed. Values of the parameters $W_0$ and $\theta_{e,0}$ can be determined. The calibration can include the steps of causing a first liquid of known refractive index to be contained in the vessel 12. A relative rotation between the vessel 12 and the position sensor 40 can then be carried out, for example, using the rotation stage 54, such that, for the first liquid, the beam of light 42 exits the exit side 18 substantially perpendicular to the beam position sensor 40 and impinges thereon at its midpoint. Accordingly, the aforementioned initial calibration value of d may be taken as 0.

The calibration method can further include recording $W_0$ and $\theta_{e,0}$, emptying the vessel 12 of the first liquid, and causing a second liquid of known refractive index to be contained in the vessel 12. The refractive index of the second liquid is different than that of the first liquid. Values of d, W and $\theta_e$ corresponding to the second liquid can then be determined, with the values of W and $\theta_e$ being respectively calculated from the equations (3) and (4) above. The temperatures of the first and second liquids can be measured, during calibration, using temperature sensor 30 such that the refractive index of each liquid is accurately determined at well-defined temperatures. Calibration can be carried out under constant temperature conditions.

The parameters L and $W_0$ can be determined as follows. The value of L can be determined by measuring the position L' of the laser beam 24 on the outside of the vessel 12 and then using Snell's law in conjunction with the vessel wall thickness t to determine the value of L as shown in FIG. 1B. One subtracts from L' the downward displacement of the beam through the entrance side 16, determined from Snell's law. Once L is known, Snell's law can again be used to determine $W_0$. Alternatively, the wall thickness t can be subtracted from $W_0^1$ to yield $W_0$. Accordingly, the values of L and $W_0$ may be determined by measurements and calculations using Snell's law. The measurements of $W_0^1$ and $L^1$ can be made with a ruler. $W_0^1$ and $L^1$ can be measured from an actual corner of a "virtual" sharp corner where the planar sides would intersect when rounded corners are present.

The present invention also provides a method for determining the concentration of a given component in a sample of a multi-component liquid mixture. The method includes the steps of determining the refractive index of the sample of the multi-component liquid mixture as described above, and then comparing the refractive index of the sample thus determined to predetermined data relating different concentrations of the given component of the multi-component liquid mixture to corresponding values of the refractive index of the multi-component mixture, so as to convert the determined refractive index of the sample to a corresponding concentration of the given component in the sample of the multi-component liquid mixture. It will be appreciated that the above-described apparatus of FIGS. 1A and 1B can be used in carrying out this method. The aforementioned comments on calibration also apply to this method.

This method can also include the additional step of recording the temperature of the sample of the multi-component liquid mixture. In this latter case, the step of comparing the refractive index of the sample of the multi-component liquid mixture to the predetermined data can include comparing the refractive index of the sample previously determined to values of the predetermined data relating the different concentrations of the given component to the corresponding values of the refractive index for at least two temperatures near the recorded temperature of the sample, and then interpolating between those values. As described above with respect to the apparatus 10, the interpolation can be carried out at the at least two temperatures near the recorded temperature of the sample of the multi-component liquid mixture, so as to obtain the value of concentration of the given component in the sample of the multi-component liquid mixture which is determined for the recorded temperature. Again, as described above, the temperature can be determined with the temperature sensor 50.

In the foregoing method, the predetermined data relating different concentrations of a given component of the multi-component liquid mixture to corresponding values of the refractive index of the multi-component liquid mixture may be double valued as described above, such that certain values of the refractive index correspond to two different values of concentration. For example, with reference to FIG. 3, refractive indices from about 1.331 to about 1.342 each correspond to two different values of methanol concentration. In this case, the method can further include storing previously measured values of concentration for the given component in the sample of the multi-component liquid mixture taken at proximate prior points in time, and then using such stored previously measured values of the concentration to indicate an expected range of a newly measured concentration value so that the correct newly measured concentration value can be selected.

The present invention further provides a method for determining a change in concentration of a given component in a sample of a multi-component liquid mixture from an initial concentration corresponding to an initial refractive index of the sample at an initial temperature. This method is advantageous for relatively small changes in concentration, as discussed above with respect to Equation (1). This method includes the steps of (a) determining the refractive index of the sample of the multi-component liquid mixture as described above; (b) determining a change in the refractive index, Δn, by subtracting the refractive index determined in the preceding step from an initial refractive index; (c) measuring the temperature of the sample of the multi-component liquid mixture, for example, with the temperature sensor 50; and (d) determining the change, ΔC, in the concentration of the given component in the sample of the multi-component liquid mixture, from the initial concentration, according to equation (1) given above.

The present invention yet further provides a method for determining the temperature of a sample of a liquid, wherein the liquid may be a pure liquid or a multi-component liquid having a substantially constant concentration of each component. The method includes the steps of (a) determining the refractive index of the sample of the liquid as described above; and comparing the determined refractive index of the sample to predetermined data which relate the different temperatures of the liquid to corresponding values of the refractive index of the liquid, so as to convert the determined refractive index to a corresponding temperature of the sample of the liquid. Again, the above-described apparatus 10 can be employed in carrying out this method. The above-described equations (2), (3) and (4) can be employed. The foregoing description of calibration of the apparatus 10 is also applicable to this method.

Further description of the theory of the present invention will now be set forth. Both absolute and relative index of refraction changes can be measured with the present invention. Extremely small changes in concentration can be resolved, on the order of 0.01 mass %, while at the same time precise measurements can be made over a large range of concentration values (0–100 mass %). The apparatus of the present invention can be readily adapted for continuous flow measurement, making it suitable for real-time monitoring and control of liquid manufacturing processes.

Concentrations may be mass percent, volume percent, or molar; mass percent is preferred. Mass concentration may be known, e.g., by measuring the mass of liquid(s) added to the vessel 12 with scale 58, so that the refractive index as a function of concentration is obtained. Conversely, if the relationship between concentration and refractive index is already known, the concentration of the mixture can be determined. The refractive index of a liquid depends on its density, as described in J. D. Spear, R. E. Russo, and R. J. Silva, "Collinear Photothermal Deflection Spectroscopy with Light-Scattering Samples," 29 *Applied Optics* 4225–34 (1990), and the wavelength of the incident light, as set forth in G. M. Hale and M. R. Querry, "Optical Constants of Water in the 200-nm to 200-μm Wavelength Region," 12 *Applied Optics* 555–63 (1973). Fluctuations in both temperature and concentration will change the liquid density (with pressure effects neglected). Thus, for an isothermal, achromatic measurement, the change of the refractive index of a multi-component liquid is determined only by the concentration of the components.

In general, the measured refractive index of a multi-component liquid mixture is a function of its temperature, T, concentration of a given component, C, and the wavelength of the incident light, λ:

$$n = n(T, C, \lambda) \quad (5)$$

From Eq. 5, the change of refractive index, Δn, of a multi-component liquid mixture is:

$$\Delta n \approx (\partial n/\partial T)\Delta T + (\partial n/\partial C)\Delta C + (\partial n/\partial \lambda)\Delta \lambda \quad (6)$$

for small changes in the temperature, concentration, and wavelength. Since laser light is highly monochromatic and wavelength-stable, Δλ≈0, and wavelength effects can be neglected. As noted, the concentration herein is preferably defined on a mass percent basis. Thus, for liquid components A and B:

$$C_A = M_A/(M_A + M_B)$$

and $$C_B = M_B/(M_A + M_B), \quad (7a, 7b)$$

where $C_A$, $C_B$ are concentration of components A and B, respectively, and $M_A$ and $M_B$ are masses of components A and B, respectively. Thus, by measuring the change in refractive index and the liquid temperature, the concentration change can be expressed using Eq. (4) above.

To measure Δn, Snell's law is employed to relate the incident and exit light beam angles, and the liquid refractive index as the beam passes through the vessel 12. For light passing from medium 1 to 2 with indices of refraction $n_1$ and $n_2$, respectively, Snell's law takes the form $$n_1 \sin \theta_1 = n_2 \sin \theta_2. \quad (8)$$

where $\theta_1$ and $\theta_2$ are the angles of the light beam in mediums 1 and 2, respectively, measured with respect to the normal to the interface of medium 1 and medium 2. In FIG. 1B, the laser beam 24 is sent into the vessel 12 at an incident angle $\theta_i$ such that it passes through the wall 16 into the material 14 and then strikes and passes through the wall 18, which may be perpendicular to the entrance wall 16. Applying Snell's law to this optical path, the exit position W and exit angle $\theta_e$ are given by equations (3) and (4) above.

Note that both $\theta_e$ and W are (in general) required, because a change in $n_1$ results in a change both in the exit angle $\theta_e$ from the vessel 12 and a translation of the beam 42 along the exit wall of the vessel 12. Both will result in a beam position change at the beam position sensor 40. The change in the beam position, d, at the sensor 40 in FIG. 1a can be expressed by equation (2) above.

In many cases, $\theta_e$ is more significant than W, and a simplified, explicit formula for the unknown refractive index $n_1$ can be used:

$$n_1 = (\sin^2\theta_i + \sin^2\theta_e)^{1/2}. \quad (9)$$

The importance of lateral beam displacement on the vessel exit side 18 (difference between W and $W_0$) decreases with increasing distance D between the vessel 12 and beam position sensor 40. For example, with D=2 cm, lateral beam displacement contributes about 4% of total beam deflection; this declines to about 1% at D=10 cm and continues to decline with increasing D.

Referring to Eq. (1), temperature changes in the liquid will result in a perceived concentration change. Rather than attempt to maintain an isothermal system, the liquid temperature can be monitored, and the concentration change can be compensated for temperature by using Eq. (1) and values of dn/dT such as those in Table 1 below. It will be seen that values of total derivative, dn/dT, are tabulated in Table 1 because the data therein is for pure liquids. Values for mixtures can be estimated by linearly interpolating, using the values of dn/dT for each component. The value of $\partial n/\partial T$ may often be approximately constant with concentration, or can be treated as a function of concentration and a double interpolation carried out.

TABLE 1

Thermo-Optical Properties of Liquids

| | n(589 nm, 20° C.) | n(632.8 nm, 20° C.) | $10^4 \times dn/dT$ (K$^{-1}$) |
|---|---|---|---|
| water | 1.3330 [17] | 1.331 [21] | −1.04 [18] |
| ethanol | 1.3614 [17] | 1.358 [21] | −3.9 [21] |
| methanol | 1.3290 [17] | 1.325 [21] | −3.9 [21] |

EXAMPLE 1

A Melles-Griot 05-LHR-111 1 mW linearly polarized HeNe laser with a wavelength of 632.8 nm served as the light source 22. A precision square glass cuvette, with interior dimensions of 10×10×35 mm, was used as the vessel 12 (and optical cell). The lengths of each cuvette side were measured and found to be nominally 10 mm with an uncertainty of ±25 µm, and the edges were square to within ±3.0 mrad. The laser beam 24 was directed onto the cuvette wall 16 at a specified incident angle ranging from 70 to 80° (measure with respect to the normal to the wall) using a rotation stage 54. The beam 42 exits the adjacent cuvette wall 18 at an angle $\theta_e$ that depends on the index of refraction, $n_1$, of the liquid in the cuvette, and the exiting beam strikes a semiconductor beam position sensor 40.

As the concentration—and hence the refractive index—of the liquid in the cuvette changes, the beam position on the sensor 40 will move accordingly. A UDT LSC-5L linear beam position sensor with a 15 V bias voltage was used as sensor 40 to monitor this position change of the beam 42. This highly linear, low noise position sensor was of the single photodiode type and was capable of detecting beam displacements as small as 2 µm. It was manufactured by United Detector Technologies, Inc. of San Jose, Calif. The sensor output was sent to a position-to-voltage converter 46, which produced an output voltage linearly proportional to the beam position. This voltage output was in turn measured using a 6.5 digit Keithley Model 2000 digital voltmeter (DVM), shown in FIG. 1A as first voltmeter 48. The measured sensor sensitivity was 3.89 mV/µm. The DVM readings were sent via a Hewlett-Packard industry standard general purpose bus (GPIB) interface to computer 44, which was a personal computer running Visual Basic for data acquisition. Typically, 10 readings were taken over a 1 sec interval and averaged to obtain a final reading.

The UDT SL5-2 beam position sensor has three leads. The center lead can be grounded while the other to leads A and B each provide a current $I_A$ and $I_B$, respectively. With the beam 42 centered on the beam position sensor 40, the same current ($I_A=I_B$) will flow in each of the leads A and B. A change in the currents will occur when the beam 42 goes off center. The currents $I_A$ and $I_B$ can be converted to respective voltages $V_A$ and $V_B$, respectively, using a well known operational amplifier technique. The differential voltage, $V_A-V_B$, directly relates to the beam position. To avoid errors in measuring caused by fluctuations in light beam intensity, the voltage difference ($V_A-V_B$) is normalized by the voltage sum ($V_A+V_B$). This can be accomplished by adding $V_A$ and $V_B$ by using a well known operational amplifier technique and by using an AD734 4-quadrant multiplier-divider manufactured by Analog Devices, Inc. of Norwood, Mass. to provide a quantity $(V_A-V_B)(V_A+V_B)$, which is also directly proportional to beam position relative to the center of the LSC-5L beam position sensor.

The concentration of the given component in the liquid (mass % concentrations were used) was determined using an Ohaus laboratory digital balance, shown in FIG. 1A as scale 54, with a resolution of 0.01 g. The glass cuvette 12 and rotation stage 54 were mounted on scale 58. Very small concentration changes that would otherwise not be resolvable with the scale 58 were made by first preparing a diluted mixture of known concentration, and then adding this diluted mixture to the cuvette, so that the total mass was large enough to be measured by the scale 58. To minimize vibration effects, the system was assembled on a vibration-isolated optical bench. Vibration isolation is believed to be desirable in all embodiments of the present invention. A 2 mm diameter thermistor was used as temperature sensor 50 and was placed under the test liquid surface inside the cuvette to monitor the liquid temperature. The liquid temperature was recorded simultaneously with the beam position using a second Keithley multimeter, shown in FIG. 1A as voltmeter 52.

To calibrate the system, two test liquids, pure water and methanol, which both have well-characterized refractive indices, were used. Calibration needs to be done only once, provided the components in the optical path of the system are not moved. The pure water was first placed in the vessel 12, and the beam position sensor 40 was oriented perpendicular to the exit laser beam 42, which impinged on the center of the sensor 40. The beam position $W_0$ and exit angle $\theta_{e,0}$ required in Eq. (2) were also recorded. Next D in Eq. (2) was determined by removing the water and adding pure methanol to the cell, which resulted in a beam displacement, d, at the beam position sensor 40. The new values of W and $\theta_e$ were determined from Eqs. (3) and (4), which allowed for determining the sole unknown, D. The liquid temperature during calibration was also measured to ensure accurate values of n.

To demonstrate the refractive index measurement capabilities of the present invention, ethanol-water and methanol-water mixtures were used, as they have refractive indices that exhibit a strong non-linear dependence on the concentration, as described in D. J. Williams, *Nonlinear Optical Properties of Organic and Polymeric Materials* (American Chemical Society, Washington, D.C., 1983), and as is well documented in the literature. For the concentration measurement (described in Example 2 below), two aqueous salt solutions, NaCl—$H_2O$ and $MgCl_2$—$H_2O$, were used, because dn/dC for such mixtures is substantially constant, which simplifies the analysis and allows for determining the smallest possible resolution of the system.

Figure 2:
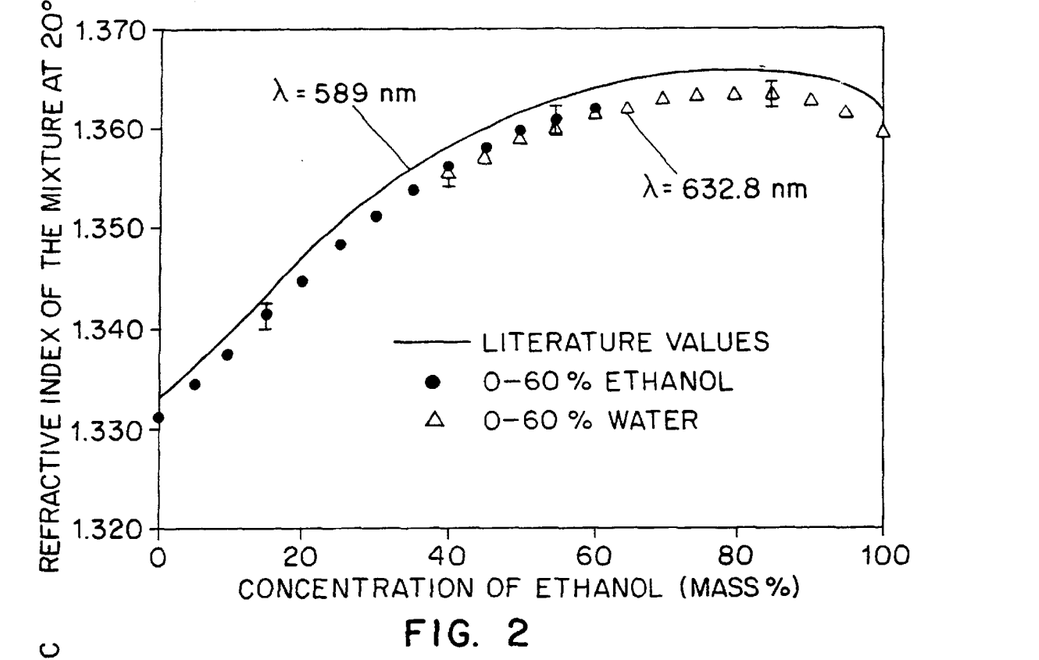
FIG. 2 is a plot of refractive index of an ethanol-water mixture versus ethanol concentration, determined using the present invention and compared to known values.

Results of measured $n_1$ for ethanol-water and methanol-water are shown in FIG. 2 and FIG. 3, respectively. Typical liquid temperatures ranged from 21–23° C., and the solid-line data values have been temperature compensated to 20° C. The concentration ranges from 0 to 100% alcohol of each liquid. Two separate sets of data from two runs appear: the first ranges from 0 to 60% alcohol (solid dots), the second from 40% to 100% alcohol (open triangles). Because concentration changes were effected by adding one liquid to another, two runs were required to obtain data that span the entire 0–100% concentration range. In one run, alcohol was added to water, starting with pure water, while in the other run, water was added to alcohol, starting with pure alcohol. It is noted that in both FIG. 2 and FIG. 3 there is very good agreement in the data from the two runs in the overlap region between 40 and 60%. The solid line is a measurement from the literature for the same liquid system, but at a wavelength of 589 nm, as described in D. R. Lide, Ed., *CRC Handbook of Chemistry and Physics* (CRC Press, Boca Raton, 1998), where the index of refraction is slightly larger. Note the agreement in the shape of the measured data with that of the published data in both figures is good. The entire concentration range (0–100%) was measured without any configuration changes or other adjustments to the system.

EXAMPLE 2

Figure 4:
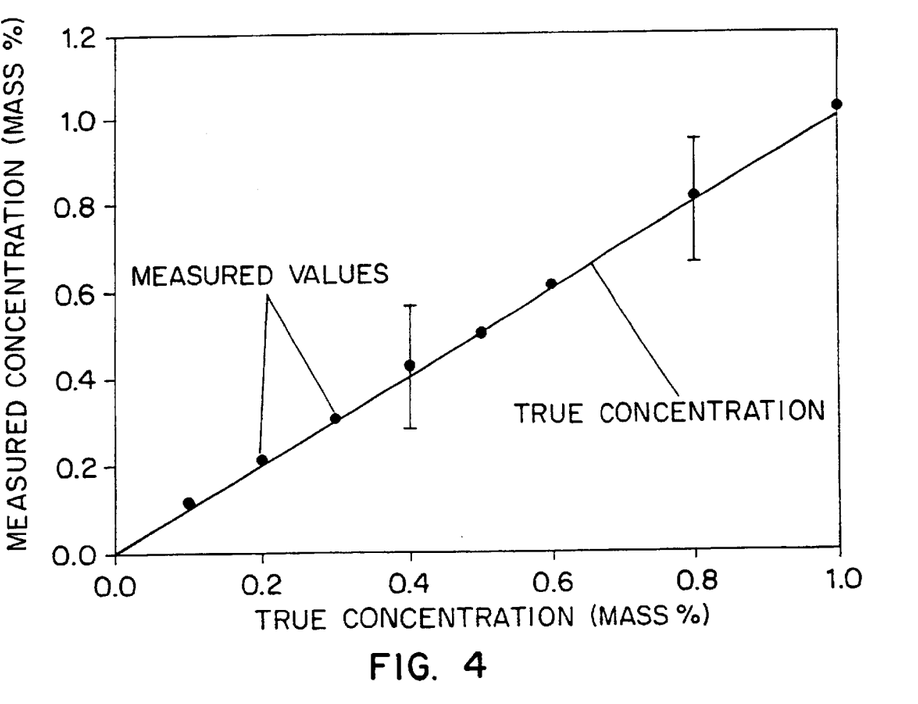
FIG. 4 is a graph of measured concentration vs. true concentration for a NaCl-water solution.
Figure 5:
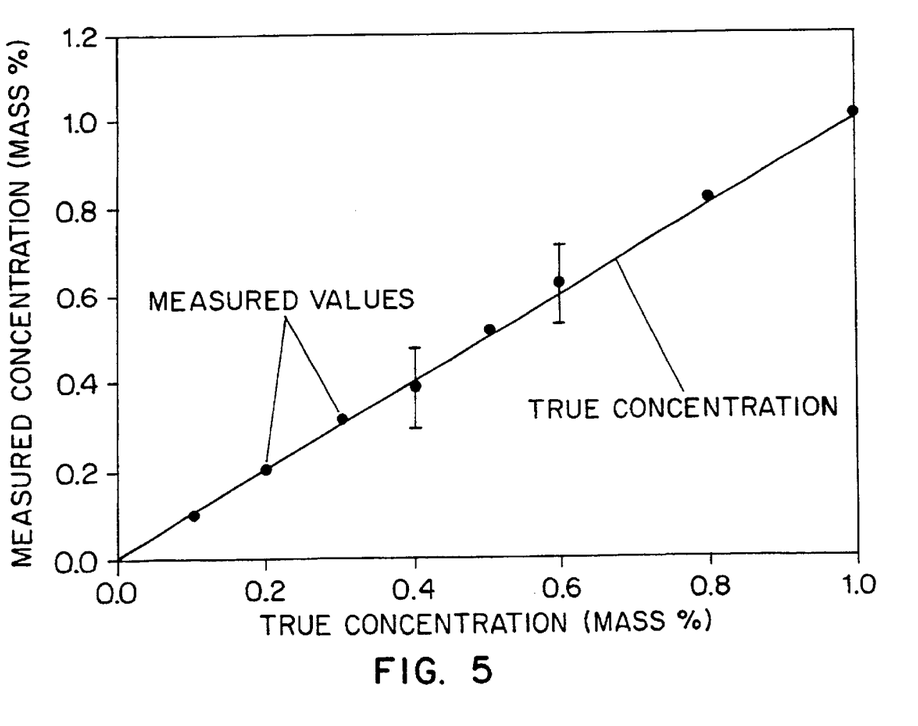
FIG. 5 is a figure similar to FIG. 4 for a MgCl$_2$-water solution.
Figure 6:
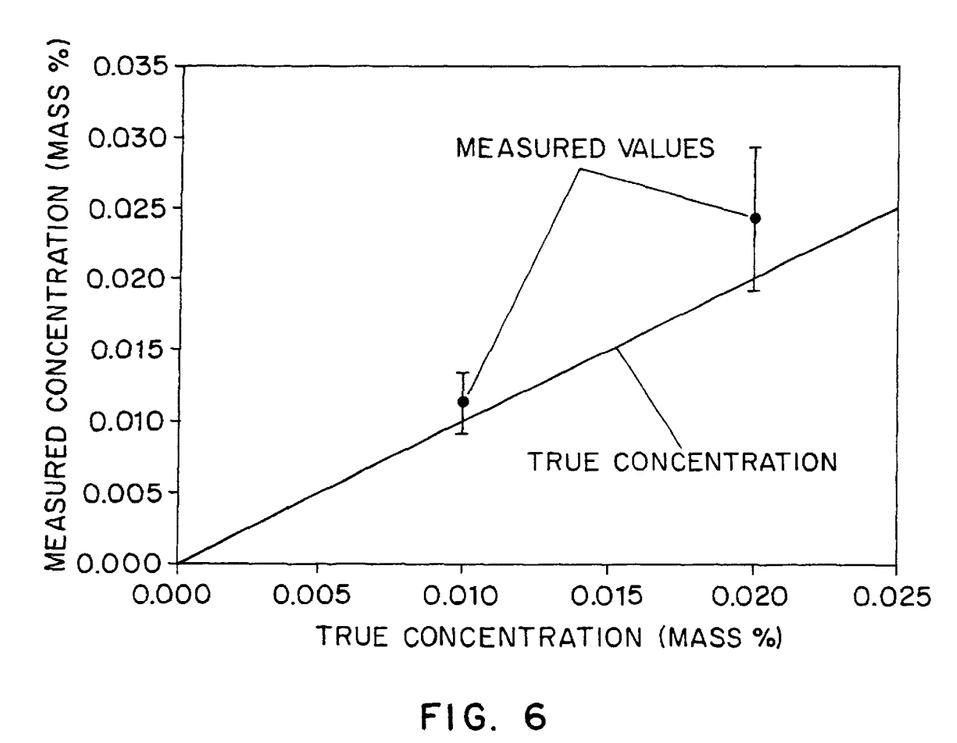
FIG. 6 is a plot similar to that of FIG. 5, but for very small concentration changes.

To measure concentration, aqueous salt solutions of NaCl and $MgCl_2$ were used. Such solutions have a substantially linear relationship between n and C, i.e., dn/dC is substantially constant, as described in D. R. Lide, Ed., *CRC Handbook of Chemistry and Physics* (CRC Press, Boca Raton, 1998). The values of dn/dC for NaCl—$H_2O$ and $MgCl_2$—$H_2O$ solutions at 20° C. are $1.71\times10^{-3}$ and $2.60\times10^{-3}$%, respectively. Measurements on aqueous salt mixtures permit very small concentration changes to be made easily, and without effects such as evaporation losses and cooling that the alcohol mixtures would incur. Known concentrations were prepared by measuring the salt on a microbalance and dissolving in a measured mass of water. Results are shown in FIG. 4 and FIG. 5 for NaCl—$H_2O$ and $MgCl_2$—$H_2O$ solutions, respectively. To illustrate the resolution of the technique in accordance with the present invention, the concentration was varied by only 1%. The results are in excellent agreement with expected values. To determine the smallest possible resolution of the technique according to the present invention, tests were run on 0.01% and 0.02% $MgCl_2$—$H_2O$ solutions. The results are shown in FIG. 6, and it can be seen that the technique according to the present invention is capable of measuring concentration changes on the order of 0.01%. All results from the technique according to the present invention are in very good agreement with the true concentration.

Uncertainties in the refractive index measurement arise from systematic errors in distance and angle measurements, and random errors such as vibration, air disturbances, and laser fluctuations. Random errors can be accounted for using statistical averaging techniques during data acquisition. Systematic errors can be determined from the following error analysis. Referring to FIGS. 1A and 1B, and Eqs. (2)–(4), uncertainties, in L, $\theta_i$, and D contribute to uncertainly in $n_1$. Error arising from the vessel wall thickness, t, vessel index of refraction (glass was used in the Examples described herein), $n_g$, and the refractive index of the two calibration liquids (water and methanol) are generally negligible. Uncertainties in L and $\theta_i$ were taken as half of the measurement instrument resolution, and are ±0.5 mm and ±0.5°, respectively. The uncertainty of the vessel-sensor distance, D, was also found to be ±0.5 mm based on the calibration procedure discussed above.

Uncertainty in W, $U_w$, can be obtained from Eq. (3) using the root-sum-square method:

$$U_w=\{[(\partial W/\partial L)U_L]^2+[(\partial W/\partial \theta_i)U_{\theta i}]^2+[(\partial W/\partial n_1)U_{n1}]^2\}^{1/2} \quad (10)$$

Similar expressions for the uncertainty in $\theta_i$ and d can be obtained from Eqs. (4) and (2), respectively. The complexity of Eqs. (2)–(4) make an explicit expression for the uncertainty in $n_1$ difficult. Thus, the uncertainty in $n_1$ was numerically solved for to derive the measured uncertainty in W and $\theta_1$. It is these results that are shown as the error bars in FIG. 2 and FIG. 3. The error bars in FIGS. 4, 5 and 6 are based on estimated wort-case uncertainties, determined as set forth above. Actual agreement is found to be better than the predicted error bars.

When determining the concentration by measuring the index of refraction, the relationship between $n_1$ and C is required. The uncertainty in C, $U_c$, is then $$U_c=(\partial n/\partial C)^{-1}(U_n) \quad (11)$$

Due to a larger value of dn/dC, the $MgCl_2$—$H_2O$ results have an uncertainty of 0.09% in FIG. 5, which is smaller than 0.14% for the NaCl—$H_2O$ solution in FIG. 4.

The thermistor used as temperature sensor 50 was calibrated in a separate temperature-controlled water bath using a NIST-traceable platinum-resistance RTD standard thermometer with a reported accuracy of 0.01° C., resulting in a thermistor uncertainty of less than 0.1° C. The power of the HeNe laser used as light source 22 was 1 mW and the absorption coefficient of the test liquids, α, is on the order of $10^{-3}$, as described in D. Solimini, "Loss Measurement of Organic Materials at 6328 Å," 37 *Journal of Applied Physics* 3314–15 (1966). Thus the contribution to heating by the laser beam is negligible. Temperature variations in the liquid were recorded and used to compensate for temperature drift of the test liquid during the measurement.

Although the present invention has been described with reference to specific exemplary embodiments, it should be understood that various changes, substitutions and alterations can be made to the disclosed embodiments without departing from the spirit and scope of the invention as defined by the appended claims.

What is claimed is:

1. A method for determining the concentration of a given component in a sample of a multi-component liquid mixture, said method comprising the steps of:
    (a) determining the refractive index of the sample of the multi-component liquid mixture by:
        (a-1) causing the sample of the liquid mixture to be contained in a vessel having a planar entrance side and a planar exit side, with a known angular relationship therebetween, said vessel being immersed in known surroundings;
        (a-2) causing a beam of light to impinge on said entrance side at an angle $\theta_i$ with respect to normal to an outer surface of said entrance side, to pass through the sample of the multi-component liquid mixture, and to then pass through said exit side, from which said beam exits at an angle $\theta_e$ with respect to a normal to an outer surface of said exit side; and
        (a-3) calculating the refractive index of the sample of the multi-component liquid mixture, based on said angles $\theta_i$ and $\theta_e$, by applying Snell's law at:
            an interface between the surroundings and said entrance side;
            an interface between said entrance side and the sample of the multi-component liquid mixture;
            an interface between the sample of the multi-component liquid mixture and said exit side; and
            an interface between said exit side and the surroundings; and
    (b) comparing the refractive index of the sample of the multi-component liquid mixture determined in step (a) to predetermined data relating different concentrations of the given component of the multi-component liquid mixture to corresponding values of the refractive index of the multi-component liquid mixture, so as to determine the concentration of the given component in the sample of the multi-component liquid mixture corresponding to the refractive index of the sample determined in step (a).

2. The method of claim 1, wherein:
step (a) further comprises the additional step of:
    (a-4) providing a beam position sensor which senses a position of said beam of light after said beam exits said exit side, and wherein step (a-3) uses said sensed position of said beam in calculating the refractive index of the sample of the multi-component liquid mixture.

3. The method of claim 2, wherein:

said entrance and exit sides of said vessel have a substantially uniform thickness and a substantially uniform refractive index; and step (a-3) comprises determining the refractive index of the given sample of the multi-component liquid mixture according to a first equation:

$$d(n_1)=[W_0-W(n_1)]\cos\theta_{e,0}+\{D-[W_0-W(n_1)]\}\tan[\theta_e(n_1)-\theta_{e,0}],$$

where:

$d(n_1)$ is the position where said beam of light impinge on said beam position sensor, relative to a reference position, $W_0$ is a reference value of distance between an inner corner formed by an intersection of said planar entrance and exit sides, and a point where said beam of light exits said exit side, determined by measurement and Snell's-law calculation when said vessel contains the reference liquid for calibration, $\theta_{e,0}$ is a reference value of said angle with respect to the normal to the surface of the exit side at which said beam of light exits said exit side, determined when the vessel contains a reference liquid for calibration, D is distance from said point where said beam of light exits said exit side to said position sensor, determined when the vessel contains the reference liquid for calibration, $W(n_1)$=is a value of said distance between said inner corner formed by the intersection of said planar entrance and exit sides, and a point where said beam of light exits said exit side, when said vessel contains the sample of the multi-component liquid mixture, defined according to a second equation:

$$W(n_1)=L\cot[\arc\sin((\sin\theta_i)/n_1)]+t\tan\{\arc\sin[(n_1/n_g)(1-(\sin\theta_i)/n_1)^{1/2}]\}$$

where:

L=distance from said inner corner to a point where said beam of light passes from said entrance side into the given sample of the multi-component liquid mixture, determined by measurement and Snell's-law calculation, $n_1$=refractive index of the sample of the multi-component liquid mixture which is to be determined, t=thickness of said entrance side and said exit side of said vessel, and $n_g$=refractive index of said entrance side and said exit side of said vessel, and $\theta_e(n_1)$ is the value of $\theta_e$, for the sample of the multi-component liquid mixture, defined according to a third equation:

$$\theta_e(n_1)=\arc\sin\{n_1\cos[\arc\sin((\sin\theta_i/n_1)]\}.$$

4. The method of claim 3, further comprising the additional step of performing calibration and measurement to determine $W_0$, $\theta_{e,0}$ D, said calibration and measurement including:

causing a first reference liquid of known refractive index to be contained in said vessel;

causing a relative rotation between said vessel and said beam position sensor such that, for the first reference liquid, said beam of light exits said exit side in a direction substantially perpendicular to said beam position sensor, whereby said beam of light impinges on the beam position sensor at the reference position;

measuring $W_0$ and recording $\theta_{e,0}$;

emptying said vessel of the first reference liquid;

causing a second reference liquid of known refractive index to be contained in said vessel, the refractive index of the second reference liquid being different than that of the first reference liquid;

determining values of d,W and $\theta_e$ corresponding to the second liquid, the values of W and $\theta_e$ being respectively calculated from said second and third equations; and using the values of d, W and $\theta_e$ in said first equation to determine D.

5. The method of claim 1, further comprising the additional step of recording the temperature of the sample of the multi-component liquid mixture, wherein step (b) comprises:

(b-1) comparing the refractive index of the given sample of the multi-component liquid mixture determined in step (a) to values of the predetermined data relating the different concentrations of the given component of the multi-component liquid mixture to corresponding values of the refractive index of the multi-component liquid mixture, for at least two temperatures near the recorded temperature of the sample of the multi-component liquid mixture; and (b-2) interpolating between the values of the predetermined data at the at least two temperatures near the recorded temperature of the sample of the multi-component liquid mixture so as to obtain an interpolated concentration of the sample of the multi-component liquid mixture.

6. The method of claim 1, wherein the predetermined data relating different concentrations of the given component of the multi-component liquid mixture to corresponding values of the refractive index of the multi-component liquid mixture are double valued, such that individual values of the refractive index in at least a portion of a given range of the corresponding values of the refractive index correspond to two different values of concentration, said method further comprising the additional steps of:

(c) storing previously measured values of concentration for the given sample of the multi-component liquid mixture taken at prior points in time, said previously measured values of concentration being indicative of the expected range of values of the concentration being determined; and (d) using the previous values of the concentration stored in step (c) to select which of the two different values of the concentration corresponding to the value of the refractive index determined in step (a) is correct.

7. A method for determining a change in concentration of a given component in a sample of a multi-component liquid mixture from an initial concentration of the given component corresponding to an initial refractive index of the sample at an initial temperature, said method comprising the steps of:

(a) determining the refractive index of the sample of the multi-component liquid mixture by:

(a-1) causing the sample of the liquid mixture to be contained in a vessel having a planar entrance side and a planar exit side, with a known angular relationship therebetween, said vessel being immersed in known surroundings;

(a-2) causing a beam of light to impinge on said entrance side at an angle $\theta_i$ with respect to a normal to an outer surface of said entrance side, to pass through the sample of the multi-component liquid mixture, and to then pass through said exit side, from which it exits at an angle $\theta_e$ with respect to a normal to an outer surface of said exit side; and (a-3) calculating the refractive index of the sample of the multi-component liquid mixture, based on said angles $\theta_i$ and $\theta_e$, by applying Snell's law at:

an interface between the surroundings and said entrance side;

an interface between said entrance side and the given sample of the multi-component liquid mixture;

an interface between the sample of the multi-component liquid mixture and said exit side; and an interface between said exit side and the surroundings:

(b) determining a change in refractive index, $\Delta n$, by subtracting from the initial refractive index the refractive index determined in step (a-3);

(c) measuring the temperature of the sample of the multi-component liquid mixture; and (d) determining the change, $\Delta C$, in the concentration of the given component in the sample of the multi-component liquid mixture from the initial concentration according to the approximate formula:

$$\Delta C \cong (\Delta n - (\partial n/\partial T)\Delta T)(\partial n/\partial C)^{-1},$$

where:

$\partial n/\partial T$ is partial derivative of index of refraction, n, with respect to temperature, determined from known data, $\Delta T$ is the difference between the temperature measured in step (c) and the initial temperature, and $\partial n/\partial C$ is partial derivative of index of refraction, n, with respect to concentration, evaluated from known data in a region near the initial concentration.

8. A method for determining the temperature of a sample of a liquid, the liquid being one of a pure liquid and a multi-component liquid mixture having a substantially constant concentration of its components, said method comprising the steps of:

(a) determining the refractive index of the sample of the liquid by:

(a-1) causing the given sample of the liquid to be contained in a vessel having a planar entrance side and a planar exit side, with a known angular relationship between said entrance side and said exit side, said vessel being immersed in known surroundings;

(a-2) causing a beam of light to impinge on said entrance side at an angle $\theta_i$ with respect to a normal to an outer surface of said entrance side, to pass through the sample of the liquid, and to then pass through said exit side, from which it exits at an angle $\theta_e$ with respect to a normal to an outer surface of said exit side; and (a-3) calculating the refractive index of the given sample of the liquid, based on said angles $\theta_i$ and $\theta_e$, by applying Snell's law at:

an interface between the surroundings and said entrance side;

an interface between said entrance side and the sample of the liquid;

an interface between the sample of the liquid and said exit side; and an interface between said exit side and the surroundings; and (b) comparing the refractive index of the given sample of the liquid determined in step (a) to predetermined data relating different temperatures of the liquid to corresponding values of the refractive index of the liquid, so as to determine the temperature of the sample of the liquid corresponding to the refractive index of the sample determined in step (a).

9. The method of claim 8, wherein:

step (a) further comprises the additional step of:

(a-4) providing a beam position sensor which senses a position of said beam of light after said beam exits said exit side, and wherein step (a-3) uses said sensed position of the beam in calculating the refractive index of the sample of the multi-component liquid mixture.

10. The method of claim 9, wherein:

said entrance and exit sides of said vessel have a substantially uniform thickness and a substantially uniform refractive index; and step (a-3) comprises determining the refractive index of the sample of the liquid mixture according to a first equation:

$$d(n_1) = [W_0 - W(n_1)]\cos\theta_{e,0} + \{D - [W_0 - W(n_1)]\}\tan[\theta_e(n_1) - \theta_{e,0}]$$

where:

$d(n_1)$ is said position where said beam of light impinges on said beam position sensor, expressed as a distance relative to a reference beam position, $W_0$ is a reference value of distance between an inner corner formed by an intersection of said planar entrance and exit sides, and a point where said beam of light exits said exit side, determined by measurement and Snell's-law calculation, $\theta_{e,0}$ is a reference value of said angle at which said beam of light exits said exit side, determined when the vessel contains a reference liquid for calibration, D is distance from said point where said beam of light exits said exit side to said beam position sensor, determined when the vessel contains the reference liquid for calibration, $W(n_1)$ = is a value of said distance between said inner corner formed by the intersection of said planar entrance and exit sides, and a point where said beam of light exits said exit side, for the sample of the liquid, defined according to a second equation:

$$W(n_1) = L \cot[\arc\sin((\sin\theta_i)/n_1)] + t\tan\{\arc\sin[(n_1/n_g)(1-(\sin\theta_i/n_1)^{1/2}]\}$$

where:

L = distance from said inner corner to a point where said beam of light passes from said entrance side into the given sample of the liquid, determined by measurement and Snell's-law calculation, $n_1$ = refractive index of the sample of the liquid which is to be determined, t = thickness of said entrance side and said exit side of said vessel, and $n_g$ = refractive index of said entrance side and said exit side of said vessel, and $\theta_e(n_1)$ is the value of $\theta_e$, for the sample of the liquid, defined according to a third equation:

$$\theta_e(n_1) = \arc\sin\{n_1 \cos[\arc\sin((\sin\theta_i/n_1)]\}.$$

11. The method of claim 10, further comprising the additional step of performing calibration and measurement to determine $W_0$, $\theta_{e,0}$ and D, said calibration and measurement including:

causing a first reference liquid of known refractive index to be contained in said vessel;

causing a relative rotation between said vessel and said position sensor such that, for the first reference liquid, said beam of light exits said exit side in a direction substantially perpendicular to said position sensor, whereby said beam of light impinges on the beam position sensor at the reference position, whereby the value of d for the beam at said reference position may be taken as zero;

measuring $W_0$ and recording $\theta_{e,0}$;

emptying said vessel of the first reference liquid;

causing a second reference liquid of known refractive index to be contained in said vessel, the refractive index of the second reference liquid being different from that of the first reference liquid;

determining values of d, W and $\theta_e$ corresponding to the second liquid, the values of W and $\theta_e$ being respectively calculated from said second and third equations; and using the values of d, W and $\theta_e$ in said first equation to determine D.

12. An apparatus for determining the concentration of a given component in a sample of a multi-component liquid mixture, said apparatus comprising:

(a) a vessel which contains said sample, said vessel having a planar entrance side and a planar exit side, with a known angular relationship between said entrance side and said exit side, said vessel being immersed in known surroundings;

(b) a light source which is located so as to cause a beam of light to impinge on said entrance side at an angle $\theta i$ with respect to a normal to an outer surface of said entrance side, to pass through said sample, and to then pass through said exit side, from which it exits at an angle $\theta e$ with respect to a normal to an outer surface of said exit side;

(c) a sensor which determines said exit angle $\theta e$, thereby permitting the refractive index of said sample to be determined, based on said angles $\theta i$ and $\theta e$, by applying Snell's law at:
      an interface between the surroundings and said entrance side;
      an interface between said entrance side and the sample;
      an interface between the sample and said exit side; and
      an interface between said exit side and the surroundings; and (d) a computer programmed to compare a refractive index of said sample determined using said angles $\theta i$ and $\theta e$ with predetermined data relating different concentrations of the given component of the multi-component liquid mixture to corresponding values of the refractive index of the multi-component liquid mixture so as to determine the concentration of the given component in the sample of the multi-component liquid mixture.

13. The apparatus of claim 12, wherein:

said sensor comprises a beam position sensor which senses a relative position of said beam of light after said beam exits said exit side, said beam position sensor having a known geometrical relationship to said vessel such that said sensed beam position can be related to said exit angle $\theta_e$.

14. The apparatus of claim 12 wherein the computer stores the predetermined data relating different concentrations of the given component of the multi-component liquid mixture to corresponding values of the refractive index of the multi-component liquid mixture.

15. The apparatus of claim 12, wherein said entrance and exit sides of said vessel have a substantially uniform thickness and a substantially uniform refractive index, said apparatus and said computer receives a representation of said position of said beam of light and which determines the refractive index of the material according to a first equation:

$$d(n_1)=[W_0-W(n_1)]\cos\theta_{e,0}+\{D-[W_0-W(n_1)]\}\tan[\theta_e(n_1)-\theta_{e,0}]$$

where:

$d(n_1)$ is said relative position of said beam of light, measured with said position sensor, relative to an initial calibration value, $W_0$ is a reference value of distance between an inner corner formed by an intersection of said entrance and exit sides, and a point where said beam of light exits said exit side, determined during calibration, $\theta_{e,0}$ is a reference value of said angle at which said beam of light exits said exit side, determined during calibration, D is distance from said point where said beam of light exits said exit side to said position sensor determined during calibration, $W(n_1)$ is a value of said distance between said inner corner formed by the intersection of said entrance and exit sides, and a point where said beam of coherent light exits said exit side, for the sample, during a given measurement, defined according to a second equation:

$$W(n_1)=L\cot[\arc\sin((\sin\theta_i)/n_1)]+t\tan\{\arc\sin[(n_1/n_g)(1-(\sin\theta_i)/n_1)^{1/2}]\}$$

where:

L=distance from said inner corner to a point where said beam of coherent light passes from said entrance side into the liquid, determined during calibration, $n_1$=refractive index of sample which is to be determined, t=thickness of said entrance side and said exit side of said vessel, and $n_g$=refractive index of said entrance side and said exit side of said vessel, and $\theta_e(n_1)$ is the value of $\theta_e$, for the liquid, during said measurement, defined according to a third equation:

$$\theta_e(n_1)=\arc\sin\{n_1\cos[\arc\sin((\sin\theta_i/n_1)]\}.$$

16. The apparatus of claim 12, wherein:

said sensor comprises a photodiode beam position sensor and a position-to-voltage converter which produces an output voltage which is substantially linearly proportional to said relative position of said beam; and said computer is a digital computer;

said apparatus further comprising:
      a first voltmeter which receives said output voltage from said position-to-voltage converter and which supplies a corresponding digital signal to said computer as said representation of said relative position of said beam of light; and
      a temperature sensor which is positioned to sense temperature of the sample of the liquid mixture and which is coupled to said computer so as to supply said computer with a digital signal representative of the temperature of the sample of the liquid mixture.

17. The apparatus of claim 16, further comprising a rotation stage which is interposed between said vessel and a mounting surface such that said relative position of said beam of light can be adjusted, during calibration of said apparatus, to be substantially perpendicular to said beam position sensor and impinging on said beam position sensor at a reference position thereof.

18. The apparatus of claim 17, further comprising a scale interposed between said rotation stage and the mounting surface, whereby changes in mass concentration of the liquid may be determined.

19. An apparatus for determining the temperature of a sample of liquid, said apparatus comprising:

(a) a vessel which contains said sample, said vessel having an entrance and an exit side, with a known angular relationship, between said entrance side and said exist side, said vessel being immersed in known surroundings;

(b) a light source which is located so as to cause a beam of light to impinge on said entrance side at an angle $\theta_i$ with respect to a normal to an outer surface of said entrance side, to pass through said sample, and to pass through said exit side, from which it exits at an angle $\theta_e$ with respect to a normal to an outer surface of said exit side;

(c) a sensor which determines said exit angle $\theta_e$ thereby permitting the refractive index of said sample to be determined, based on said angle $\theta_i$ and $\theta_e$, by applying Snell's law which:
an interface between the surrounding and said entrance side;
an interface between said entrance side and the sample;
an interface between the sample and said exit side; and
an interface between said exit side and the surroundings;

(d) a computer programmed to compare a refractive index of said sample determined using said angles $\theta_i$ and $\theta_e$ with predetermined data relating different temperatures of the liquid to corresponding values of the refractive index of the liquid so as to determine the temperature of the sample of the liquid.

20. The apparatus of claim 19 wherein the computer stores the predetermined data relating different temperatures of the liquid to corresponding values of the refractive index of the liquid.

21. The apparatus of claim 12, wherein said computer is programmed to perform the comparison of the determined refractive index to values of the predetermined data for at least two temperatures near the temperature of the liquid mixture and to interpolate between the values of the predetermined data at the at least two temperatures so as to correct the value of the concentration of the given component in the sample of the multi-component liquid mixture for the temperature of the sample of the liquid mixture.

22. The apparatus of claim 12, wherein said computer stores previously measured values of concentration of the given component in the sample of the multi-component liquid mixture taken at prior points in time and said computer is programmed to employ the previously measured values to indicate an expected range of concentrations of the given component to permit the selection of a correct value of concentration when concentration is double-valued with respect to index of refraction.

23. The apparatus of claim 12, further comprising:

a temperature sensor which is positioned to sense temperature of the sample of the multi-component liquid mixture and which is coupled to said computer so as to supply said computer with a signal representative of the temperature of the multi-component liquid;

wherein:
said computer is programmed to determine the refractive index of a given sample of the multi-component liquid mixture, based on said angles $\theta_i$ and $\theta_e$, by applying Snell's law at:
an interface between the surroundings and said entrance side;
an interface between said entrance side and the sample of the multi-component liquid mixture;
an interface between the sample of the multi-component liquid mixture and said exit side; and
an interface between said exit side and the surroundings;

and;

said computer is also programmed to determine a change in refractive index of the multi-component liquid mixture, $\Delta n$, by subtracting, from the refractive index determined by said computer using Snell's law, an initial refractive index of the sample of the multi-component liquid mixture at an initial concentration of the given component in the sample and at an initial temperature of the sample measured with said temperature sensor, to receive said signal which represents the temperature of the sample of the multi-component liquid mixture under test, and to determine the change, $\Delta C$, in the concentration of the given sample of the multi-component liquid mixture from the initial concentration according to the approximate formula:

$$\Delta C \cong (\Delta n - (\partial n/\partial T)\Delta T)(\partial n/\partial C)^{-1},$$

where:
$\partial n/\partial T$ is partial derivative of index of refraction, n, with respect to temperature, determined from known data,
$\Delta T$ is the difference between the temperature of the sample of the multi-component liquid mixture under test and the initial temperature, and
$\partial n/\partial C$ is partial derivative of the index of refraction, n, with respect to concentration, evaluated from known data in a region near the initial concentration.

* * * * *

UNITED STATES PATENT AND TRADEMARK OFFICE
CERTIFICATE OF CORRECTION

PATENT NO. : 6,549,276 B1  Page 1 of 1
DATED : April 15, 2003
INVENTOR(S) : Longtin; Jon P.

It is certified that error appears in the above-identified patent and that said Letters Patent is hereby corrected as shown below:

Column 16,
Line 44, "dn/dC" should read -- $\partial n/\partial C$ --

Column 17,
Lines 8 and 11, "dn/dC" should read -- $\partial n/\partial C$ --

Column 18,
Line 1, "dn/dC" should read -- $\partial n/\partial C$ --

Column 19,
Line 12, "impinge" should read -- impinges --
Line 29, "W($n_1$)=is" should read -- W($n_1$) is --
Line 48, "and" should be deleted

Column 22,
Line 43, "W($n_1$)=is" should read -- W($n_1$) is --

Column 24,
Line 6, "claim 12" should read -- claim 13 --
Lines 8-9, "said apparatus and" should be deleted
Line 27, "sensor determined" should read -- sensor, determined --

Column 25,
Line 20, "exist" should read -- exit --

Signed and Sealed this

Thirtieth Day of March, 2004

JON W. DUDAS
*Acting Director of the United States Patent and Trademark Office*